United States Patent [19]

Furst et al.

[11] Patent Number: 4,828,842

[45] Date of Patent: May 9, 1989

[54] WATER DISPERSIBLE COMPOUND

[75] Inventors: Gene A. Furst, Allegan; Dennis E. Allen; Peter C. Altamore, all of Allegan, Mich.

[73] Assignee: L. Perrigo Company, Allegan, Mich.

[21] Appl. No.: 907,813

[22] Filed: Sep. 16, 1986

[51] Int. Cl.$^4$ .................... A61K 9/14; A61K 35/78
[52] U.S. Cl. .................... 424/480; 424/195.1; 424/482
[58] Field of Search .................... 424/195.1, 480, 482

[56] References Cited

U.S. PATENT DOCUMENTS

| | | | |
|---|---|---|---|
| 1,891,697 | 12/1932 | Tuvin | 424/195.1 |
| 1,891,698 | 12/1932 | Tuvin | 424/195.1 |
| 2,043,204 | 6/1936 | Spalding | 167/56 |
| 2,278,464 | 4/1942 | Musher | 167/56 |
| 2,820,741 | 1/1958 | Endicott et al. | 167/82 |
| 3,455,714 | 7/1969 | Bishop et al. | 106/205 |
| 4,143,163 | 3/1979 | Hutchison et al. | 426/96 |
| 4,198,400 | 4/1980 | Biegler | 424/180 |
| 4,321,263 | 3/1982 | Powell et al. | 424/195 |
| 4,459,280 | 7/1984 | Colliopoulos et al. | 424/35 |
| 4,511,561 | 4/1985 | Madaus et al. | 424/195.1 |
| 4,543,370 | 9/1985 | Porter et al. | 523/100 |
| 4,548,806 | 10/1985 | Colliopoulos et al. | 424/35 |
| 4,551,331 | 11/1985 | Rudin | 424/195.1 |
| 4,678,516 | 7/1987 | Alderman et al. | 106/197.1 |
| 4,683,256 | 7/1987 | Porter et al. | 524/285 |

Primary Examiner—Shep K. Rose
Attorney, Agent, or Firm—Price, Heneveld, Cooper, DeWitt & Litton

[57] ABSTRACT

The specification discloses a dietary bulking agent comprising psyllium powder, Aspartame TM and a coating of a blend of hydroxypropyl methylcellulose with a minor amount of polyethylene glycol.

19 Claims, No Drawings

WATER DISPERSIBLE COMPOUND

BACKGROUND OF THE INVENTION

The present invention relates to bulk forming laxative products. These are typically based on psyllium or an equivalent fibrous vegetable material Such products typically include sugar which facilitates dispersion of the fibrous vegetable material in water so that it can be consumed. However, dispersion is a serious problem in sugar-free fibrous vegetable bulking products. The fibrous material simply does not disperse adequately in water.

U.S. Pat. No. 4,321,263 to Powell et al, issued Mar. 23, 1982 and entitled "PSYLLIUM COMPOSITIONS," wets the psyllium with a minimum of 2% of either polyethylene glycol or polyvinypyrrolidone and alleges that the resulting psyllium composition is substantially instantly dispersible in water. The patent indicates that other polymeric materials such as hydroxypropyl methylcellulose (Methocel E-15 TM), carboxyvinyl polymer (Carbopol TM), polyoxyethylene/-polyoxypropylene block copolymer (Pluronic F-68 TM) and polyvinylmethylmethacrylate (Gantrez-AN119 TM) do not facilitate dispersion of psyllium. Powell teaches that psyllium coated with hydroxypropyl methylcellulose, where the coating comprises 1% of the composition, requires 90 seconds to wet and disperse and at 2% requires 120 seconds to wet and disperse.

SUMMARY OF THE INVENTION

In the present invention, a fibrous, vegetable material is coated with a combination of a major amount of hydroxypropyl methylcellulose and a minor amount of polyethylene glycol. Surprisingly, fibrous vegetable material coated with the foregoing combination wets and disperses essentially instantaneously when placed on water.

These and other aspects and features of the invention will be more fully understood and appreciated by reference to the written specification and appended claims.

DESCRIPTION OF THE PREFERRED EMBODIMENT

In the preferred embodiment, the actual coating of the present invention comprises from about 0.1 to about 2% by weight of the total fibrous bulking composition. Most preferably, the coating is at a level of about 0.5%. The product comprises a small amount of artificial sweetner, as for example 0.25% Aspartame TM. (Aspartame TM is the dipeptide of 1-phenylalanine and 1-aspartic acid.) The rest is the fibrous vegetable material itself.

The coating of the present invention comprises 85 to 95% hydroxypropyl methylcellulose and 5 to 15% polyethylene glycol. The most preferable combination is about 90% hydroxypropyl methylcellulose and about 10% polyethylene glycol. These percentages and all of the percentages set forth herein are by weight unless otherwise specifically stated. The coating is applied to the fibrous vegetable material as about a 5% solution in alcohol with a minor amount of water.

The most preferable fibrous vegetable material comprises psyllium powder. Psyllium powder comprises the ground husks of the seed of the plantago ovata plant species. The husks consist principally of the colorless epidermis of mucilage containing cells. Any similarly powdered fibrous vegetable material which serves as a bulking agent and for which dispersion in water does not readily occur naturally could also be used in the present invention.

Preferably, the psyllium powder is of a 20 to 200 mesh (U.S. Series Sieve) particle size. The precise particle size distribution for a preferred psyllium useful in the present invention is set forth in Table I below:

| U.S. Series Seive Mesh No. | Percent By Weight of Powdered Psyllium Remaining on Screen |
|---|---|
| 20 | 0 |
| 30 | 10.3 |
| 40 | 23.9 |
| 60 | 47.2 |
| 80 | 12.8 |
| 100 | 2.9 |
| 200 | 2.7 |
| Pan | .2 |

As can be seen by reference to Table I, it can be said that the psyllium most preferably comprises from about 20 to about 80 mesh particle distribution since the bulk of the material falls within that screen range.

The density of a suitable psyllium powder loose is approximately 0.44 grams per cubic centimeter. Tapped, the same material has a density of 0.50 grams per cubic centimeter.

To coat the psyllium powder, a solution is prepared comprising 90 parts by weight of a 1 to 4 carbon alcohol, 10 parts by weight of deionized water and 5 parts by weight of the coating composition. The most preferable alcohols are ethanol and isopropyl alcohol. While some variation in the percentage of coating composition in the foregoing solution is acceptable, the foregoing proportions are preferred.

The coating process can best be explained by the following example:

EXAMPLE 1

1,000 grams of psyllium powder, 20 to 80 mesh, is placed in a suitable mixer with 2.53 grams of Aspartame TM. 105 grams of an alcohol/water solution of the preferrd coating composition (90% hydroxypropylmethyl cellulose and 10% polyethylene glycol) is introduced into the mixer, with mixing in order to wet the psyllium powder. Mixing is continued for 5 minutes. The wetted psyllium is then emptied from the mixer and dried. The resulting composition has the following formula:

| Ingredient | Percent |
|---|---|
| Psyllium Powder (20/80 mesh) | 99.25% |
| Aspartame TM | .25% |
| Coating Composition (90/10) | .50% |

Of course, other mixing and coating techniques can be used as will be appreciated by those skilled in the art.

TEST RESULTS

To test the dispersive effectiveness of the bulking agent of the present invention, the preferred embodiment psyllium powder was coated with a preferred embodiment coating (90/10) to a level of 0.10%, 0.25%, 0.50% and 2%. One teaspoonful (rounded) of the coated psyllium powder was placed on the surface of a 400 ml beaker of water without stirring. The time required for the coated psyllium powder to wet and disperse completely was determined. The average dispersion times for several samples are indicated in Table II below:

TABLE II

| Percentage Coating | Average Dispersion Time |
| --- | --- |
| .10 | 3.83 seconds |
| .25 | 4.10 seconds |
| .50 | 4.20 seconds |
| 2.00 | 5.13 seconds |

The foregoing results compare favorably with a commercially available bulking agent sold under the trademark "Metamucil TM." In a similar test, a teaspoonful of sugar-free Metamucil TM was not fully dispersed until the passage of more than three minutes. Furthermore, the results set forth in Table II are strikingly superior to the results reported in U.S. Pat. No. 4,321,263 to Powell, where it is indicated that at a 1% coating level, a psyllium powder coated with hydroxypropylmethyl cellulose requires 90 seconds to disperse and coated at the 2% level requires 120 seconds to disperse.

It is curious to note that at the 0.10% coating level, the product of the present invention actually seems to disperse more rapidly. Yet with no coating, psyllium powder does not even disperse satisfactorily with stirring. Accordingly, the 0.50% coating level is preferred in order to insure that a proper coating is achieved under commercial production conditions.

Naturally, the foregoing constitutes a preferred embodiment of the invention. Various changes and alterations may be apparent to those skilled in the art and can be made without departing from the spirit and broader aspects of the invention as set forth in the appended claims.

The embodiments of the invention in which an exclusive property or privilege is claimed are defined as follows:

1. A dietary bulk supplement comprising:
    a fibrous, vegetable material powder which is not naturally dispersable in water, coated with a blend of a major amount of hydroxypropyl methylcellulose and a minor amount of polyethylene glycol.
2. The dietary supplement of claim 1 in which said coating comprises 0.10 to 2% of the product.
3. The dietary supplement of claim 2 in which said hydroxypropyl methylcellulose comprises from about 85 to about 95% of said coating and said polyethylene glycol comprises from about 5 to about 15% of said coating.
4. The dietary supplement of claim 3 in which said fibrous vegetable material powder comprises substantially from about 20 to about 80 mesh (U.S. Series Seive) particle size.
5. The dietary supplement of claim 4 in which said fibrous vegetable material comprises psyllium powder.
6. The dietary supplement of claim 3 in which said fibrous vegetable material comprises psyllium powder.
7. The dietary supplement of claim 2 in which said fibrous vegetable material comprises psyllium powder.
8. The dietary supplement of claim 2 in which said fibrous vegetable material powder comprises substantially from about 20 to about 80 mesh (U.S. Series Seive) particle size.
9. The dietary supplement of claim 8 in which said fibrous vegetable material comprises psyllium powder.
10. The dietary supplement of claim 1 in which said hydroxypropyl methylcellulose comprises from about 85 to about 95% of said coating and said polyethylene glycol comprises from about 5 to about 15% of said coating.
11. The dietary supplement of claim 10 in which said fibrous vegetable material powder comprises substantially from about 20 to about 80 mesh (U.S. Series Seive) particle size.
12. The dietary supplement of claim 11 in which said fibrous vegetable material comprises psyllium powder.
13. The dietary supplement of claim 1 in which said fibrous vegetable material powder comprises substantially from about 20 to about 80 mesh (U.S. Series Seive) particle size.
14. The dietary supplement of claim 13 in which said fibrous vegetable material comprises psyllium powder.
15. The dietary supplement of claim 1 in which said fibrous vegetable material comprises psyllium powder.
16. A sugar-free, dietary food supplement bulking agent comprising:
    psyllium powder, a minor amount of artificial sweetener and a coating on said psyllium powder comprising a blend of a major amount of hydroxypropyl methylcellulose and a minor amount of polyethylene glycol.
17. The dietary supplement of claim 16 in which said coating comprises 0.10 to 2% of the product.
18. The dietary supplement of claim 17 in which said hydroxypropyl methylcellulose comprises from about 85 to about 95% of said coating and said polyethylene glycol comprises from about 5 to about 15% of said coating.
19. The dietary supplement of claim 18 in which said psyllium powder is from about 20 to about 80 mesh (U.S. Series Seive).

* * * * *